UNITED STATES PATENT OFFICE
CERTIFICATE OF CORRECTION

Page 2 of 3

Patent No. 4,124,601                    Dated 7 November 1978

Inventor(s) Herman W. Smith

It is certified that error appears in the above-identified patent and that said Letters Patent are hereby corrected as shown below:

Column 51, line 46, -- -$PGF_2$, -- should read "$PGF_1$,".
Column 59, line 59, -- saturatd -- should read "saturated".
Column 62, line 31, -- $\xi$ -- should read "$\delta$".
Column 62, line 50, -- $\xi$ -- should read "$\delta$".
Column 64, lines 20-21, -- 9-deoxy6,9-epoxy-5-iodo-$PFG_1\alpha$ -- should read "9-deoxy-6,9-epoxy-5-iodo-$PGF_1\alpha$".
Column 64, line 37, -- abouve -- should read "above".
Column 64, line 64, -- este -- should read "ester".
Column 65, line 25, -- 5.75 -- should read "5.57".
Column 65, line 26, -- 0.9 $\epsilon$;-- should read " 0.9 $\delta$ ;".
Column 65, line 27, -- 1315, 1190, -- should read " 1315, 1255, 1190,".
Column 65, line 58, -- -$PGF_1$ -- should read "-$PGE_1$".
Column 65, line 59, -- -$PGF_1$ -- should read "-$PGE_1$".
Column 66, line 24, -- n-pentyl, is -- should read "n-pentyl, $R_{36}$ is".
Column 66, line 46, -- stirred or 27 hr., -- should read "stirred for 27 hr.,".
Column 66, line 49, -- yield 3.75 g. -- should read "yield 3.72 g.".
Column 66, line 62, -- 3,03-3.46 -- should read " 3.03-3.46".
Column 66, line 65, -- 594.009, -- should read "594.099,".
Column 67, line  9, -- 1,1-3.35 -- should read "1.1-3.35".
Column 67, line 39, -- 1,1-3.18 -- should read "1.1-3.18".
Column 67, line 43, -- -epoxy-$14_1\alpha$, -- should read " -epoxy-14-bromo-$PGF_1\alpha$,".
Column 69, line 23, -- 1.1-3,5 -- should read "1.1-3.5".
Column 69, line 44, -- sodium carbonate -- should read " sodium bicarbonate".

OPTIONALLY SUNBSTITUTED 3-(CYANOPHENYL)BENZOFURANS

This is a division of application Ser. No. 724,719 filed Sept. 20, 1976, now U.S. Pat. No. 4,048,323, which in turn is a continuation-in-part of application serial No. 616,275, filed Sept. 24, 1975 now abandoned.

FIELD OF THE INVENTION

This invention relates to a class of 3-phenylbenzofuran compounds which are substituted on the 3 or 4 position of the phenyl ring by a carboxylic acid group and pharmaceutically acceptable salts thereof.

BACKGROUND OF THE INVENTION

3-Phenylbenzofuranylalkanoic acids and -alkenoic acids and certain derivatives thereof have been reported, for example in U.S. Pat. Nos. 3,682,976 and 3,862,134 as having antiinflammatory activity. The compound 2-nitro-3-phenylbenzofuran has been reported, although no physiological activity has been reported prior to the present invention. Certain neutral 2-nitrobenzofurans are known as antibacterial agents, for example, see French Pat. No. 2,081,585 and several publications by Rene Royer, et al. Acidic compounds combining the structural features of the compounds of the present invention have not previously been described.

SUMMARY OF THE INVENTION

The present invention relates to optionally substituted (2-nitro-3-benzofuranyl)benzoic acids and pharmaceutically acceptable salts thereof which are active as antimicrobial agents.

It is therefore an object of the invention to provide compounds which are active antimicrobial agents.

It is a further object of the invention to provide processes for preparing the compounds of the invention.

It is a further object of the invention to provide a method for controlling microbes.

It is a further object of the invention to provide a method for controlling bacteria.

It is a further object of the invention to provide a method for controlling fungi.

It is a further object of the invention to provide a method for controlling protozoa.

It is a further object of the invention to provide a method for controlling trichomonads.

It is another object of the invention to provide antimicrobial compositions containing (2-nitro-3-benzofuranyl) benzoic acids and pharmaceutically acceptable salts thereof as active ingredients therein.

It is another object of the invention to provide novel intermediates in the preparation of the antimicrobial agents of the invention and processes using the novel intermediates to prepare the active agents.

Still other objects of the invention will be made apparent by the following specification.

DETAILED DESCRIPTION OF THE INVENTION

The present invention relates to a class of compounds of the formula:

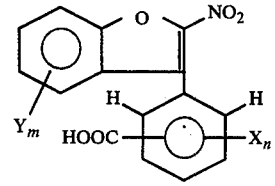

wherein X is fluorine, chlorine, lower alkyl or lower alkoxy, Y is methyl, methoxy, fluorine or chlorine and $m$ and $n$ are independently 0, 1 or 2 and pharmaceutically acceptable salts thereof. When $m$ or $n$ is 0, the indicated ring positions are unsubstituted. The term "lower" whenever used in this specification indicates groups containing from one to four carbon atoms.

The free acids are ordinarily white or yellowish to brown crystalline or amorphous materials when purified. They are substantially insoluble in water or aliphatic hydrocarbons and are more soluble in lower alcohols, halogenated solvents, benzene, dimethylformamide and the like. The alkali metal salts have appreciable solubility in water and lower alcohols.

All of the compounds of the invention are active against bacteria and some are also active against other microorganisms. including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animals. The free acids are presently preferred for many purposes due to their generally higher levels of antimicrobial activity in vitro. For applications in which water solubility is of importance, the salts are ordinarily used.

Presently preferred subclasses (due to their high degree of antimicrobial activity) are the compounds in which $m$ and $n$ are zero and the compounds in which the four (4) position of the benzofuran moiety is substituted by hydrogen. The preferred compounds are antimicrobial in vitro and in vivo, are active when administered orally and provide detectable and antimicrobially active blood levels in mammals. Some of them are active at concentrations of less than 1.0 $\mu$g/ml versus *Streptococci*. The particularly preferred compounds (which have broad spectra of antimicrobial activity and good therapeutic ratios, $LD_{50}/ED_{50}$) are 3-(2-nitro-3-benzofuranyl)benzoic acid and 4-(2-nitro-3-benzofuranyl)benzoic acid.

Alkali metal, alkaline earth, aluminum, iron and other metal and amine salts are often the equivalents of the corresponding acid-form compounds, and offer advantages in solubility, absorption, persistence, formulation and the like. The salts are of particular interest for topical use, for example in opthalmic and dermatologic formulations. The alkali metal salts (e.g., the sodium and potassium salts) are presently preferred.

The free acid compounds of the invention are prepared by several methods using known starting materials including:

A. directly nitrating the 2 position of a compound of the formula by hydrolysis of the cyano group to the carboxylic acid group. The (chloro- and bromo-3-phenyl)benzofurans are prepared, for example, by reaction of chloro- and bromo-α-bromoacetophenones with optionally substituted phenols followed by cyclization e.g., in polyphosphoric acid.

The reaction of the halogen of (chloro- or bromo-3-phenyl)benzofurans with cyanide is generally carried out in a basic organic solvent such as pyridine or quinoline. The preferred cyanide is cuprous cyanide. Elevated temperatures of 100° to 250° C are used to obtain satisfactory rates of reaction, although the temperature used should not be so high as to decompose the benzofuran ring.

Hydrolysis of the cyano group may be carried out under basic or acidic conditions. The extent of hydrolysis to the desired product is readily determined since the product is an acid and has significantly different solubility properties than the starting material.

The preparation of compounds wherein X or Y is chlorine requires that the halogen to be replaced by cyano be more reactive than chlorine, i.e., bromine, or that an alternative synthetic route be chosen.

The intermediate compounds of the formula

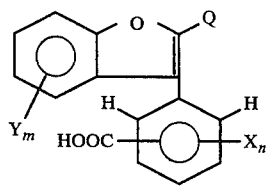

wherein Q is hydrogen, bromine or iodine are novel.

The salts of the free acid compounds of the invention are readily prepared by reaction of the acid with a base and evaporation to dryness. The base used to prepare the salts may be organic, e.g., sodium methoxide or an amine, or inorganic. Furthermore, other salts which are not pharmaceutically acceptable may be useful for the synthesis of the free acid compounds or other acceptable salts or other useful intermediates such as esters. The free acids can also be prepared from the corresponding esters by methods known to those skilled in the art.

The antimicrobial activity of the compounds is evaluated using a variation of the original agar-plate diffusion method of Vincent and Vincent (e.g., see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative bacteria. The procedure provides information on the amount of a compound required to give complete inhibition, partial inhibition or no inhibition of microbial growth on agar plates. The microbial growh on each plate is read visually, and minimal inhibitory concentrations are recorded.

The microorganisms used are: *Staphylococcus aureus, Bacillus subtilus, Pseudomonas aeruginosa, Escherichi coli, Streptoccocus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity one or more of the above microorganisms. The compounds maintain high activity against the microorganisms either in the absence or presence of ten percent horse serum.

The in vivo antimicrobial activity is determined against infections produced by *Streptococcus pyogenes* C-203, and *Staphylococcus aureus* (Smith) or other bacterial species. The species used is determined by the in vitro antimicrobial spectrum of the compound. Groups of 5 or 10 mice, 18–22 g., are infected intraperitoneally with the test culture. Treatment consists of three oral injections 1, 6 and 24 hours after infection. All mice are observed for extended periods, e.g., for 2 weeks and deaths recorded at daily intervals. Control groups consist of one infected, nontreated group and other infected groups receiving varying dosages of the reference standard.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing an object to be treated therein, or by local application to an infected area. The amount of compound to be used for, e.g., oral treatment of a microbial infection will be an effective amount less than a toxic amount. The amount to be administered to a subject and route of administration to control an infection will depend on the species of organism, the sex, weight, physical condition of the patient, the locus of the infection and many other factors, but this judgment is well within the skill of the art. Usually the amount will be less than 100 mg/kg per dose. Conveniently the oral treatment is administered in the form of one of the usual pharmaceutical preparations such as capsules, tablets, emulsions, solutions, suppositories and the like. Excipients, fillers, coatings, etc., are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

Certain of the compounds are also active antiparasitics as shown by activity in laboratory tests versus the protozoan *Trichomonas sp.* In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. Thus, while the majority of the examples relate to the free acid compounds, the other compounds of the invention can also be prepared. The melting points are uncorrected, the temperatures are in de-

EXAMPLE 1

Step A

A mixture of 40.5 g (0.43 mole) of phenol, 100 g (0.428) of 4-chloro-α-bromoacetophenone, 100 g (0.725 mole) of potassium carbonate and 500 ml of glyme is heated to its reflux temperature and maintained at reflux for about 6 hours. The reaction mixture is evaporated to remove the solvent. The residue is diluted with water and diethyl ether and the layers are separated. The ether layer is washed with water and saturated sodium chloride solution and dried over magnesium sulfate. The ether solution is evaporated to provide a dark oil which gradually solidifies on cooling. The solid is recrystallized from ethanol to provide 4-chloro-α-phenoxyacetophenone, m.p. 81°–86° C.

Step B

A mixture of 350 g of polyphosphoric acid and 51.3 g (0.208 mole) of 4-chloro-α-phenoxyacetophenone is heated to a temperature of about 80° C and maintained at this temperature for about 1 hour. The reaction mixture is then poured into cold water. The yellow product is collected, washed with water, and dissolved in diethyl ether. The ether solution is washed with cold dilute sodium hydroxide solution, water and saturated sodium chloride solution, then dried over sodium sulfate. The solvent is evaporated to provide a dark oil which solidifies to 3-(4-chlorophenyl)benzofuran. The structural assignment is supported by infrared spectral analysis.

Step C

A mixture of 45.2 g (0.198 mole) of 3-(4-chlorophenyl)benzofuran, 22.2 g (0.248 mole) of cuprous cyanide and 15 ml of pyridine is heated to 220° C. and maintained at this temperature for 1 day. The reaction mixture is poured into a solution of 47.5 g of ferric chloride, 30 ml of concentrated hydrochloric acid, and 135 ml of water with stirring. The mixture is stirred with heating below its boiling point for 1 hour. The aqueous mixture is removed and the organic portion is mixed with 1.2 1 of benzene and the mixture is stirred for 1 hour. The mixture is then filtered. The filtrate is washed with 6N hydrochloric acid, water, 10% sodium hydroxide solution and saturated sodium chloride solution then dried over magnesium sulfate. The benzene solution is then evaporated to provide a dark oil which solidifies to provide 3-(4-cyanophenyl)benzofuran. The infrared spectrum of the product is consistent with the assigned structure.

Step D

A mixture of 24.4 g (0.111 mole) of 3-(4-cyanophenyl)benzofuran, 25 g of 85% potassium hydroxide and 250 ml of 95% aqueous ethanol is heated to its reflux temperature and maintained at reflux for 15 hours. The solvent is removed by evaporation and the residue is diluted with water and diethyl ether. A solid precipitate is separated and dissolved in 800 ml of hot water. This aqueous solution is then acidified with 6N hydrochloric acid to provide a white precipitate which is collected by filtration and washed with water. The product is then recrystallized from 1,2-dichloroethane to provide 4-(3-benzofuranyl)benzoic acid, m.p. 222°–225° C.

| Analysis: | %C | %H |
| --- | --- | --- |
| Calculated for $C_{15}H_{11}O_3$: | 75.6 | 4.24 |
| Found: | 75.6 | 4.10 |

Step E

A stirred solution of 14 g (0.059 mole) of 4-(3-benzofuranyl)benzoic acid and 1500 ml of 1,2-dichloroethane which has been heated to its reflux temperature and slowly cooled to about 60° C is treated dropwise with 9.4 g (0.059 mole) of bromine diluted with 7 ml of 1,2-dichloroethane. After stirring the mixture for about 50 hours at about 55° C. the reaction mixture is cooled and the solid precipitate is collected and rinsed with 1,2-dichloroethane. Infrared spectral analysis of the crude product, 4-(2-bromo-3-benzofuranyl)benzoic acid, is consistent with the assigned structure. The crude product has a melting point of 218°–220° C.

Step F

A mixture of 18.7 g (0.059 mole) of 4-(2-bromo-3-benzofuranyl)benzoic acid and 1200 ml of acetic acid is warmed to 65° C and 7.5 g (0.089 mole) of cyclohexene is added, then 8.2 g (0.089 mole) of dinitrogen tetroxide diluted with 20 ml of acetic acid is added dropwise. After stirring for about 3 hours, the reaction mixture is poured into cold water and the solid precipitate is collected and washed with water and petroleum ether. The product is recrystallized from a mixture of N,N-dimethylformamide and water and from glyme and water. The product is 4-(2-nitro-3-benzofuranyl)benzoic acid, m.p. 274°–278° C.

| Analysis: | %C | %H | %N |
| --- | --- | --- | --- |
| Calculated for $C_{15}H_9NO_5$: | 63.6 | 3.2 | 4.9 |
| Found: | 63.2 | 3.2 | 5.2 |

Example 2

Using the method of Example 1 and starting in Step A with 3-chloro-α-bromoacetophenone and phenol and proceeding through Step D one obtains as the product of Step D 3-(3-benzofuranyl)benzoic acid, m.p. 188°–191° C.

| Analysis: | %C | %H |
| --- | --- | --- |
| Calculated for $C_{15}H_{10}O_3 \cdot \frac{1}{2}H_2O$: | 74.2 | 4.36 |
| Found: | 74.4 | 4.50 |

The product of Step E is 3-(2-bromo-3-benzofuranyl)benzoic acid, crude melting point 212°–220° C.

The product of Step F is 3-(2-nitro-3-benzofuranyl)benzoic acid, m.p. 233°–243° C.

| Analysis: | %C | %H | %N |
| --- | --- | --- | --- |
| Calculated for $C_{15}H_9NO_5$: | 63.6 | 3.2 | 4.95 |
| Found: | 63.7 | 3.6 | 4.50 |

Using the method of Example 1, Steps A through D and starting with appropriate substituted α-bromoacetophenones and substituted phenols as shown in Table I the substituted (3-benzofuranyl)benzoic acids shown are prepared.

Using the method of Example 1, Steps E and F and starting with substituted (3-benzofuranyl)benzoic acids

Table I

| Example No. | Starting Materials | Intermediate Product |
|---|---|---|
| 3 | 4-chlorophenacyl bromide + 2,3-dimethylphenol | 4-(6,7-dimethyl-3-benzofuranyl)benzoic acid |
| 4 | 4-chlorophenacyl bromide + 4-fluorophenol | 4-(5-fluoro-3-benzofuranyl)benzoic acid |
| 5 | 4-bromophenacyl bromide + 4-methoxyphenol | 4-(5-methoxy-3-benzofuranyl)benzoic acid |
| 6 | 3-bromo-4-methylphenacyl bromide + phenol | 2-methyl-4-(3-benzofuranyl)benzoic acid | the following final product compounds of the invention are prepared.

Table II

| Example No. | Starting Materials | Product |
|---|---|---|
| 7 | 4-(6,7-dimethyl-3-benzofuranyl)benzoic acid | 4-(6,7-dimethyl-2-nitro-3-benzofuranyl)benzoic acid |

Table II-continued

| Example No. | Starting Materials | Product |
|---|---|---|
| 8 | 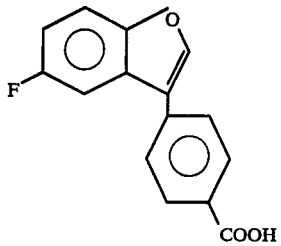 | 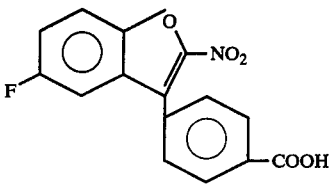 |
| 9 | 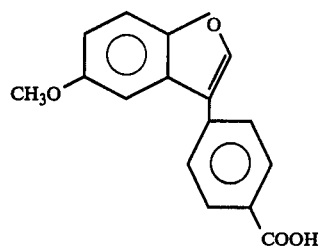 | 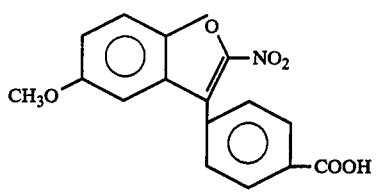 |
| 10 | 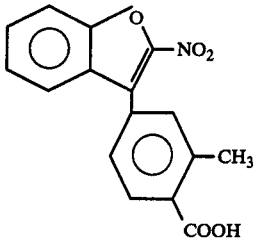 | 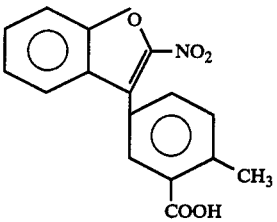 |

EXAMPLE 11

Starting with α-bromo-4-chloro-3-carbethoxyacetophenone and phenol and using the procedure of Steps A and B of Example 1 one obtains ethyl 5-(3-benzofuranyl)-2-chlorobenzoate. Steps D, E and F then lead to 2-chloro-5-(2-nitro-3-benzofuranyl)benzoic acid.

EXAMPLE 12

In a manner similar to that of Example 11, starting with ethyl 5-(α-bromoacetyl)-2-methoxybenzoate and p-chlorophenol one obtains 2-methoxy-5-(5-chloro-2-nitro-3-benzofuranyl)benzoic acid.

What is claimed is:

1. A compound of the formula

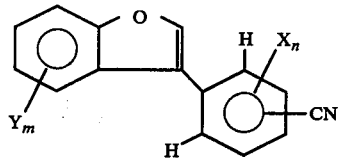

wherein X is fluorine, chlorine, lower alkyl or lower alkoxy and Y is methyl, methoxy, fluorine or chlorine and $m$ and $n$ are independently 0, 1 or 2.

2. 3-(4-Cyanophenyl)benzofuran according to claim 1.